United States Patent
Li et al.

(10) Patent No.: US 11,794,163 B1
(45) Date of Patent: Oct. 24, 2023

(54) METAL-ORGANIC FRAMEWORK FOR ADSORPTIVE SEPARATION OF ACETYLENE/ETHYLENE MIXTURE AND PREPARATION METHOD THEREFOR

(71) Applicant: TONGJI UNIVERSITY, Shanghai (CN)

(72) Inventors: Fengting Li, Shanghai (CN); Yifan Gu, Shanghai (CN); Hengcong Huang, Shanghai (CN); Ying Wang, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 0 days.

(21) Appl. No.: 18/093,407

(22) Filed: Jan. 5, 2023

(30) Foreign Application Priority Data

Jun. 9, 2022 (CN) .......................... 202210649033.3

(51) Int. Cl.
*B01J 20/22* (2006.01)
*B01D 53/04* (2006.01)
(Continued)

(52) U.S. Cl.
CPC ........ *B01J 20/226* (2013.01); *B01D 53/0423* (2013.01); *B01J 20/281* (2013.01); *B01J 20/28052* (2013.01); *B01J 20/3085* (2013.01); *B01J 20/3092* (2013.01); *C07C 7/12* (2013.01); *C07F 15/045* (2013.01);
(Continued)

(58) Field of Classification Search
CPC .... B01J 20/22; B01J 20/226; B01J 20/28052; B01J 20/281; B01J 20/3085; B01J 20/3092; B01J 2220/52; B01D 53/0423; B01D 2253/204; B01D 2257/7022; B01D 2259/4009; C07C 7/12; C07F 15/045
See application file for complete search history.

(56) References Cited

FOREIGN PATENT DOCUMENTS

| CN | 112844321 A | * | 5/2021 | ............. B01D 53/02 |
| WO | WO-2021006964 A1 | * | 1/2021 | ............. B01J 20/226 |

\* cited by examiner

*Primary Examiner* — In Suk C Bullock
*Assistant Examiner* — Jason Y Chong
(74) *Attorney, Agent, or Firm* — Locke Lord LLP; Tim Tingkang Xia, Esq.

(57) ABSTRACT

The present invention provides a metal-organic framework material for the adsorptive separation of acetylene/ethylene mixture and preparation method therefor. The metal-organic framework material is named TJE-2 with a chemical formula of $[Ni(pyc)(apyz)]_n$, wherein, Ni represents nickel as a metal center, pyc represents the organic ligand 1H-pyrazole-4-carboxylic acid, and apyz represents the organic ligand 2-aminopyrazine. The preparation method is as follows: thoroughly dissolving pyc, apyz and $Ni(NO_3)_2 \cdot 6H_2O$, transferring the mixture to a pressure-resistant closed container for heating reaction, followed by solvent exchange and activation to obtain a homogeneous powder material. The ultra-microporous metal-organic framework material prepared by the present invention features a significantly high $C_2H_2$ adsorption capacity, good selectivity, and low raw material costs, and therefore can realize $C_2H_2/C_2H_4$ separation at lower costs.

10 Claims, 5 Drawing Sheets

(51) Int. Cl.
*C07C 7/12* (2006.01)
*B01J 20/30* (2006.01)
*B01J 20/281* (2006.01)
*B01J 20/28* (2006.01)
*C07F 15/04* (2006.01)

(52) U.S. Cl.
CPC .................. *B01D 2253/204* (2013.01); *B01D 2257/7022* (2013.01); *B01D 2259/4009* (2013.01); *B01J 2220/52* (2013.01)

METAL-ORGANIC FRAMEWORK FOR ADSORPTIVE SEPARATION OF ACETYLENE/ETHYLENE MIXTURE AND PREPARATION METHOD THEREFOR

CROSS-REFERENCE TO RELATED PATENT APPLICATION

This non-provisional application claims priority to and the benefit of, pursuant to 35 U.S.C. § 119(a), patent application Serial No. CN 202210649033.3 filed in China on Jun. 9, 2022. The disclosure of the above application is incorporated herein in its entirety by reference.

TECHNICAL FIELD

The present invention relates to the field of novel materials for adsorptive gas separation, specifically to a metal-organic framework material for adsorptive separation of acetylene/ethylene mixture, and preparation method therefor.

BACKGROUND

As an important raw chemical material for a variety of polymers, ethylene ($C_2H_4$) is mainly produced by steam cracking. The ethylene product prepared by such technology generally contains about 1% of acetylene ($C_2H_2$). However, the concentration of $C_2H_2$ in $C_2H_4$ used in the production of polymers is required to be less than 40 ppm, because the presence of $C_2H_2$ can poison the catalyst and reduce the quality of polyethylene. In addition, $C_2H_2$ is an important raw material for producing a variety of polymers and can also be used as fuel. Therefore, the separation of $C_2H_2$ from $C_2H_4$ is one of the most important industrial processes.

Ethylene and acetylene are highly similar in physical properties, such as molecular size ($C_2H_2$, 3.32×3.34×5.70 Å$^3$; $C_2H_4$, 3.28×4.18×4.84 Å$^3$) and boiling point ($C_2H_2$, 188.4 K; $C_2H_4$, 169.4 K). Therefore, conventional methods such as the hydrogenation of acetylene using a noble metal catalyst often suffers from high costs and low selectivity. The solvent extraction method will generate a large amount of organic waste. Cryogenic distillation requires higher equipment construction costs and energy consumption. At present, adsorptive separation based on porous materials is an emerging technology for reducing the energy consumption required for $C_2H_2/C_2H_4$ separation.

Metal-organic frameworks (MOFs) are a novel class of microporous materials formed by the coordination and self-assembly of the metal center and organic ligands with adjustable pore size and pore chemistry, showing great application potential in the separation of $C_2H_2$ from $C_2H_4$. The Chinese Patent Application No. 201910860492.4 disclosed a method for preparing an ultra-microporous metal-organic framework material for separating acetylene from ethylene, but the synthesis of the azine ligand used in this method required severe conditions and high costs. The Chinese Patent Application No. 201810373233.4 disclosed a Cu-based metal-organic framework material, but the acetylene adsorption capacity was limited. In addition, the research on the selective adsorption of $C_2H_2/C_2H_4$ by MOFs is still on the laboratory scale, and it is difficult to ensure their high adsorption selectivity and high stability in industrial applications. To solve the above problems, the present invention is proposed.

SUMMARY

In response to the above problems, the present invention provides a metal-organic framework material for the adsorptive separation of acetylene/ethylene mixture and a method for its preparation. The ultra-microporous metal-organic framework material prepared by the present invention features a significantly high $C_2H_2$ adsorption capacity, good selectivity, high stability and low precursors costs, and therefore can realize $C_2H_2/C_2H_4$ separation at lower costs.

The present invention provides the following technical solutions:

The metal-organic framework material is named TJE-2 with a chemical formula of $[Ni(pyc)(apyz)]_n$, wherein, Ni represents nickel as the metal center, pyc represents the organic ligand 1H-pyrazole-4-carboxylic acid (structural formula:

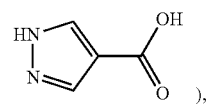

), and apyz represents the organic ligand 2-aminopyrazine (structural formula:

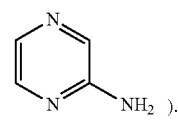

).

Distinctively, TJE-2 has ultra-microporous periodic one-dimensional channels, and the pore diameter of the channel is 4.3-6 Å. Each Ni in TJE-2 is 6-coordinated without forming open metal sites, coordinating with two N and two O atoms from the ligand 1H-pyrazole-4-carboxylic acid and with two N atoms from 2-aminopyrazine. Electronegative oxygen atoms, pyrazine rings and amino groups are distributed on the channel surface.

The present invention provides the method for preparing the metal-organic framework material, including the following steps:

S1: the organic ligand 1H-pyrazole-4-carboxylic acid and 2-aminopyrazine are dissolved in an organic solvent under stirring, then the $Ni(NO_3)_2 \cdot 6H_2O$ is added into the solution and thoroughly dissolved by stirring or ultrasonic vibration;

S2: the mixture obtained in step Si is transferred to a pressure-resistant closed container, and heated to 80-100° C. for 24-48 h;

S3: after the reaction is finished and the reaction solution is cooled to room temperature, the homogeneous powder material is obtained by filtration. Then it is solvent exchanged with methanol;

S4: the material is filtrated once again, and heated under vacuum at 80-100° C. for 24-48 h to completely remove solvent molecules in the channels. Then the activated TJE-2 is obtained.

Further, in step S1, the molar ratio of the organic ligand 1H-pyrazole-4-carboxylic acid, the organic ligand 2-aminopyrazine, and $Ni(NO_3)_2 \cdot 6H_2O$ is 1:1-2:1-5.

Further, in step S1, the organic solvent is composed of methanol and N,N-dimethylformamide, and the volume ratio of methanol to N,N-dimethylformamide is 1:0.5-2.

Further, the closed container in step S2 is a closed glass reaction bottle with a polytetrafluoroethylene mat or a polytetrafluoroethylene-lined reaction kettle.

Further, in step S3, the solvent exchange is performed for not less than 4 days and not less than 8 times.

Further, in the filtration processes in steps S3 and S4, a glass sand core suction filtration device or a Buchner funnel equipped with an organic-phase filter membrane with a pore size of 0.2-0.8 μm is used.

The present invention further provides a method for the adsorptive separation of an acetylene/ethylene mixture using TJE-2, including the following steps:

A1: activated TJE-2 is loaded in a fixed bed adsorption column with an inner diameter of 6-10 mm. Then a $C_2H_2/C_2H_4$ mixture at a flow rate of 2-10 mL/min is introduced at ambient temperature and pressure;

A2: allowing the TJE-2 to adsorb and capture the $C_2H_2$, thus the $C_2H_2$ is separated from $C_2H_4$. The high-purity $C_2H_4$ gas can be obtained in one step from the exit of the adsorption column;

A3: after the TJE-2 reaches uptake capacity, regeneration of TJE-2 is achieved by desorption under vacuum for 2-8 h or by heating and purging with inert gas.

Further, the volume ratio of the $C_2H_2/C_2H_4$ mixture can be 1:99 to 99:1.

The beneficial technical effects of the present invention are as follows:

(1) The metal-organic framework material TJE-2 prepared by the present invention has one-dimensional ultra-microporous channels, and the cross-sectional diameter of the channel is 4.3-6 Å. Oxygen atom sites, pyrazine rings and amino functional groups are distributed on the channel surface. The oxygen atom and pyrazine ring can form hydrogen bonds or it-bond interactions with $C_2H_2$, and the presence of amino functional groups can further reduce the pore size. The synergistic effect of these functional groups leads to the selective adsorptive separation effect of TJE-2 on $C_2H_2$.

(2) The present invention provides a novel method for the adsorptive separation of $C_2H_2/C_2H_4$ based on a metal-organic framework material. The novel ultra-microporous TJE-2 used in the method has a special channel and exhibits a higher adsorption capacity for $C_2H_2$ than for $C_2H_4$. Due to the different molecular configurations, $C_2H_2$ and $C_2H_4$ form different hydrogen-bond interactions in the channel. Thereby, efficient separation of the $C_2H_2/C_2H_4$ mixture can be achieved, and $C_2H_4$ gas with a purity of higher than 99.9% can be obtained.

(3) In TJE-2 obtained by the present invention, Ni coordination is saturated, and the two pyrazole N atoms from the ligand 1H-pyrazole-4-carboxylic acid both coordinate with Ni. Therefore, the metal-organic framework material has no open metal sites and can remain stable in water. In addition, the thermal decomposition temperature of the material is about 300° C., exhibiting good thermal stability.

(4) Compared with conventional porous adsorbents, the metal-organic framework material used in the present invention has the advantages of high adsorption capacity, excellent recyclability, high adsorption selectivity, and low material costs. The material used can be prepared by a simple and safe method, with a high yield and essentially no by-products.

(5) The separation method provided in the present invention features lower costs and higher selectivity than conventional hydrogenation of acetylene using a noble metal catalyst; Compared with the traditional solvent extraction method, the output of waste is smaller and the regeneration energy consumption is lower; compared with the traditional cryogenic distillation method, it has the advantages of mild operating conditions, low energy consumption and small equipment investment. Therefore, the present invention is expected to bring economic benefits to relevant petrochemical enterprises.

BRIEF DESCRIPTION OF THE DRAWINGS

To describe the technical solutions in the embodiments and prior art solutions of the present invention more clearly, the following is a brief description of the drawings that need to be used in the description of the embodiments or prior art. The drawings in the following description are only some embodiments of the present invention, and other drawings may be obtained from these drawings without creative labor for those of ordinary skill in the art.

DETAILED DESCRIPTION

The following describes the present invention in detail concerning the accompanying drawings and examples. Apparently, the embodiments described are merely some rather than all of the embodiments of the present application. All other embodiments obtained by those of ordinary skill in the art without creative efforts based on the embodiments of the present invention shall fall within the protection scope of the present invention.

EXAMPLE 1

112 mg of 1H-pyrazole-4-carboxylic acid (pyc) and 95 mg of 2-aminopyrazine (apyz) were weighed and dissolved in 30 mL of MeOH/DMF (i.e., a mixture of methanol and N,N-dimethylformamide, with a volume ratio of 1:1). Then, 290 mg of nickel nitrate hexahydrate was added and thoroughly dissolved by ultrasonic vibration. The mixture was transferred to a 50 mL sealed glass reaction vial, heated to 80° C., and reacted for 24 h. After cooling, the reaction solution was filtered using a glass sand core suction filtration device equipped with an organic phase filter membrane with a pore size of 0.22 μm, and then solvent-exchanged with methanol for 5 days. The solvent was changed twice a day, and 30 mL of fresh methanol was used each time. At last, the powder sample obtained from suction filtration was heated to 80° C. and dried for 24 h in a vacuum oven to obtain activated TJE-2.

Figure 1:
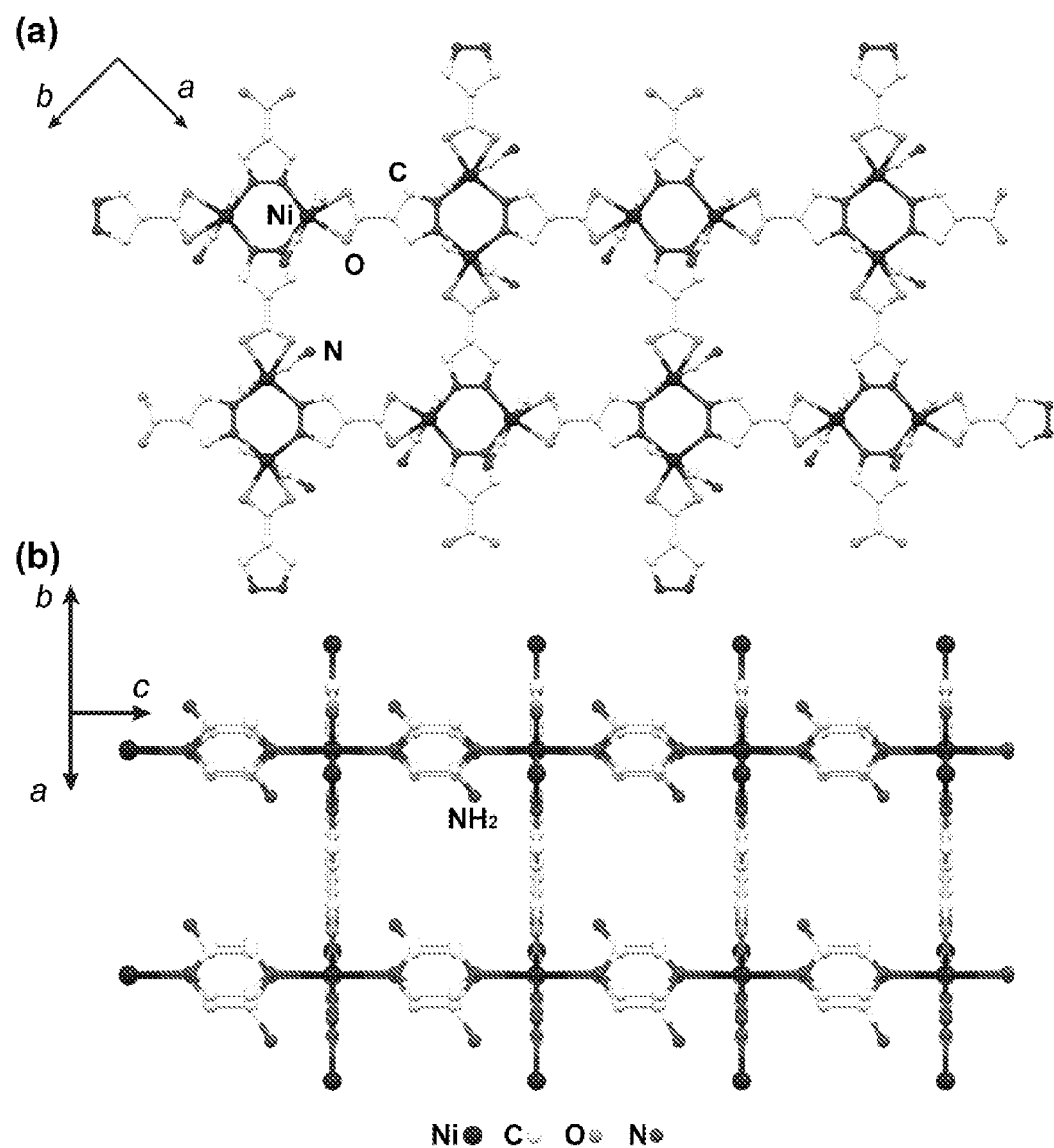
FIG. 1 is a schematic diagram showing the spatial structure of TJE-2 (where a and b are views observed from two different perspectives).
Figure 2:
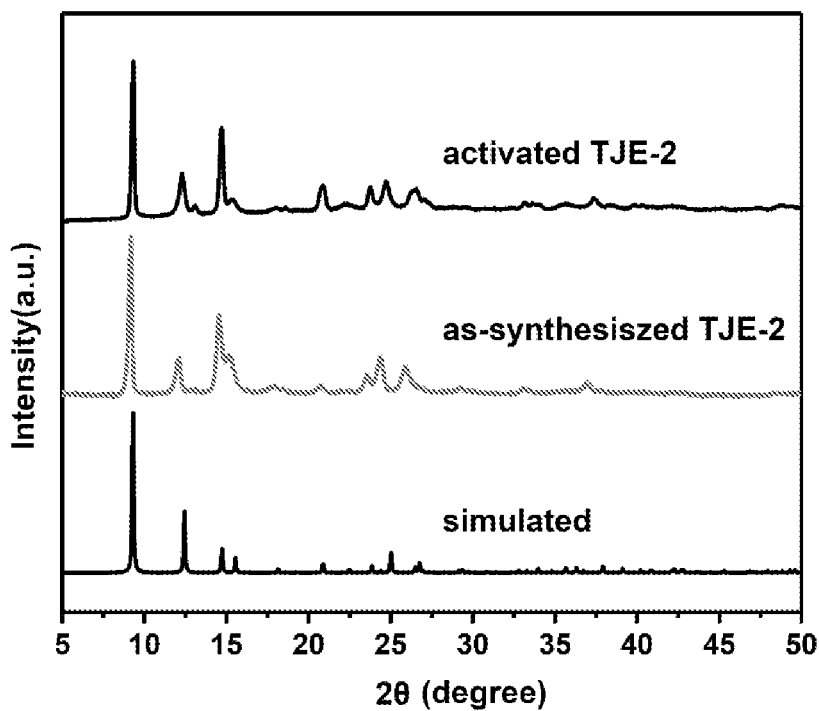
FIG. 2 shows the powder X-ray diffraction pattern for TJE-2 prepared in Example 1.
Figure 3:
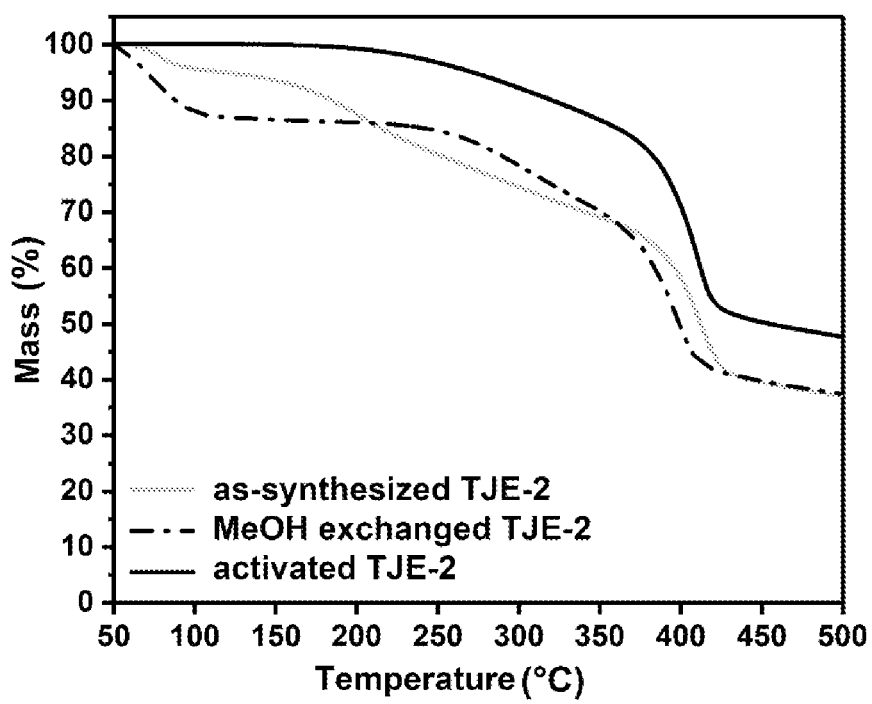
FIG. 3 shows the thermogravimetric curves of TJE-2 prepared in Example 1.

The spatial structure of TJE-2 is shown in FIG. 1. The powder X-ray diffraction results were consistent with the simulated result (FIG. 2). The thermogravimetric curves of the material before and after activated (FIG. 3) show that the material has been fully activated.

Figure 4:
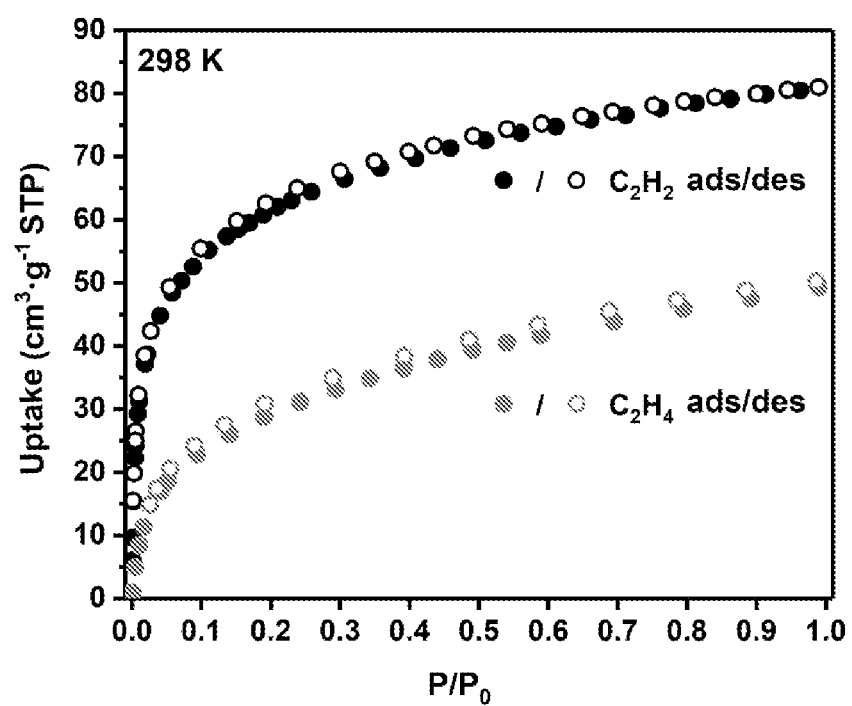
FIG. 4 shows sorption isotherms of TJE-2 prepared in Example 1 for $C_2H_2$ and $C_2H_4$ at 298 K.
Figure 5:
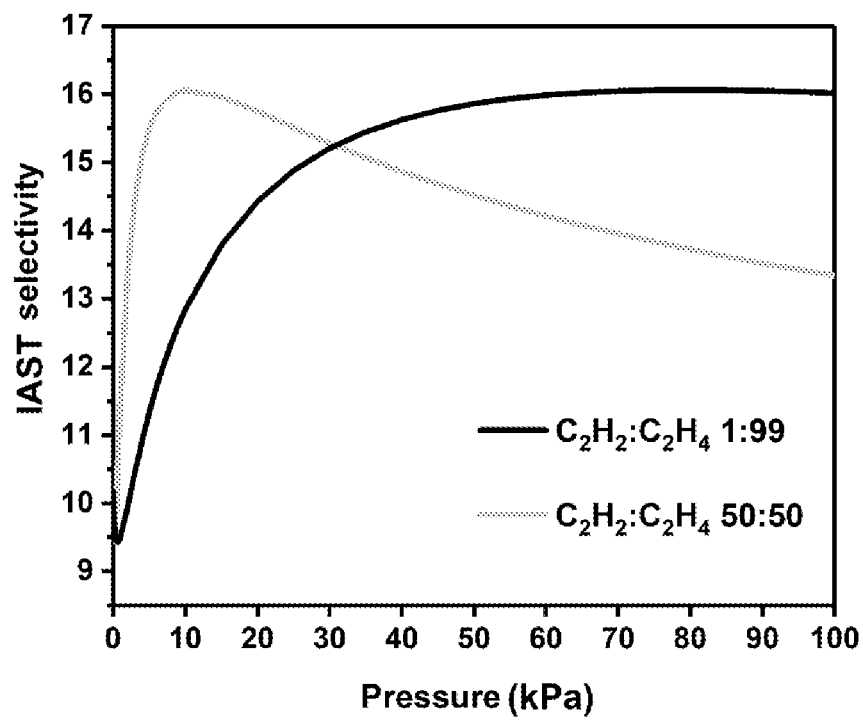
FIG. 5 shows the IAST selectivity of TJE-2 prepared in Example 1 for $C_2H_2/C_2H_4$ mixture with the ratio of 50:50 and 1:99 at 298 K.

Sorption isotherms of activated TJE-2 for $C_2H_2$ and $C_2H_4$ at 298 K were measured, as shown in FIG. 4. The adsorption capacity of TJE-2 for $C_2H_2$ (81.1 cm$^3$·g$^{-1}$) was significantly higher than that for $C_2H_4$ (49.2 cm$^3$·g$^{-1}$). As calculated using the ideal adsorbed solution theory (IAST), the ideal adsorption selectivities of TJE-2 for $C_2H_2/C_2H_4$ with a ratio of 50:50 and 1:99 at 298 K were 13.3 and 16.0, respectively (FIG. 5), indicating that TJE-2 has the adsorptive separation ability for $C_2H_2/C_2H_4$.

Figure 6:
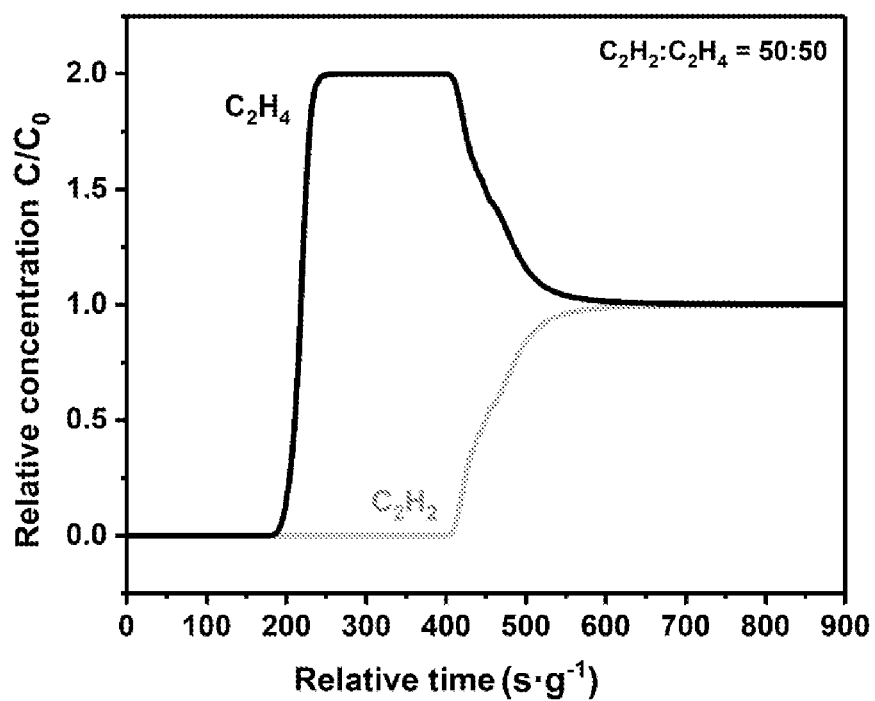
FIG. 6 shows a breakthrough curve of TJE-2 prepared in Example 1 for a $C_2H_2/C_2H_4$ mixture (with a volume ratio of 50:50) at 298 K.

0.8 g of the activated TJE-2 material was loaded into an 8 mm fixed bed adsorption column for fixed bed penetration experiments. At 298 K and 1 bar, a $C_2H_2/C_2H_4$ mixture with a volume ratio of 50:50 was introduced at a total flow rate of 10 mL/min. $C_2H_4$ gas with a purity of >99.9% was obtained directly from the outlet of the adsorption column (FIG. 6). After the adsorption of $C_2H_2$ is saturated, the adsorption column was purged with helium at 80° C. to achieve the desorption of $C_2H_2$ and the recycling of TJE-2.

EXAMPLE 2

112 mg of 1H-pyrazole-4-carboxylic acid (pyc) and 190 mg of 2-aminopyrazine (apyz) were weighed and dissolved in 30 mL of MeOH/DMF (with a volume ratio of 1:2). Then, 1.45 g of nickel nitrate hexahydrate was added and thoroughly dissolved by ultrasonic vibration. The mixture was transferred to a 50 mL closed polytetrafluoroethylene reactor, heated to 90° C., and reacted for 36 h. After cooling, the reaction solution was filtered using a Buchner funnel equipped with an organic phase filter membrane with a pore size of 0.6 μm, and then solvent-exchanged with methanol for 4 days. The solvent was changed twice a day, and 30 mL of fresh methanol was used each time. The resulting solution after suction filtration was heated to 90° C. for 36 h in a vacuum oven to obtain activated TJE-2.

Figure 7:
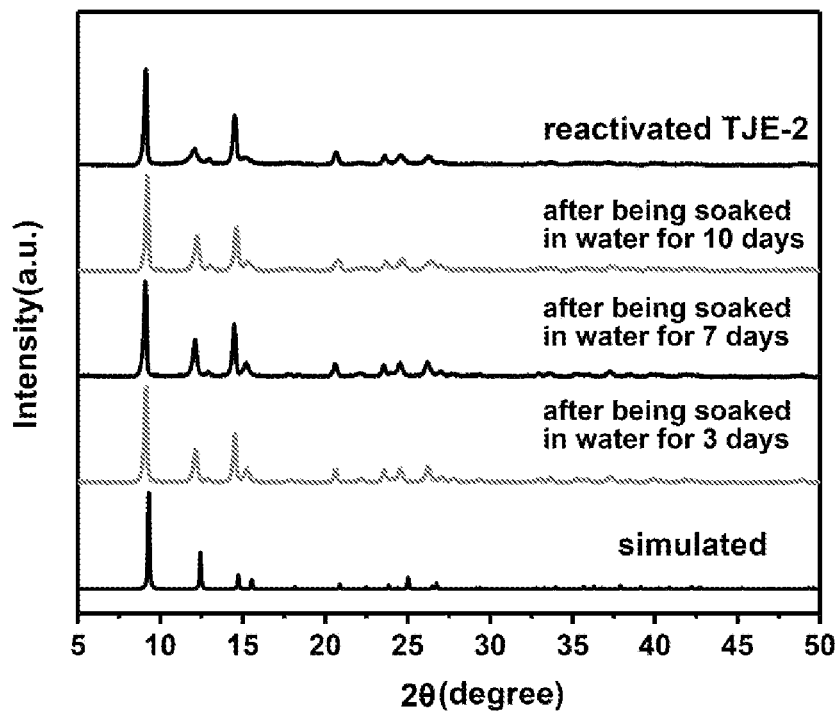
FIG. 7 shows the powder X-ray diffraction pattern for TJE-2 prepared in Example 2 and after soaking in water.

0.2 g of the activated TJE-2 material was soaked in 20 mL of water. After 10 days, the material was dried at 100° C. for 24 h under vacuum. The results of powder X-ray diffraction for the material remained unchanged throughout the process and were consistent with the simulated result, indicating that TJE-2 has excellent water stability (FIG. 7).

EXAMPLE 3

Example 3 provides a scale-up synthesis with gram-scale yield. 3.36 g of 1H-pyrazole-4-carboxylic acid (pyc) and 2.85 g of 2-aminopyrazine (apyz) were weighed and dissolved in 800 mL of MeOH/DMF (with a volume ratio of 1:0.5). Then, 17.4 g of nickel nitrate hexahydrate was added and thoroughly dissolved by ultrasonic vibration. The mixture was transferred to a 1 L closed glass reaction bottle, heated to 100° C., and reacted for 48 h. After cooling, the reaction solution was filtered using a glass sand core suction filtration device equipped with an organic phase filter membrane with a pore size of 0.8 μm, and then solvent-exchanged with methanol for 5 days. The solvent was changed three times a day, and 100 mL of fresh methanol was used each time. The resulting solution after suction filtration was heated to 100° C. for 48 h in a vacuum oven to obtain activated TJE-2. The mass of the activated material was weighed to be 6.85 g, and the yield (calculated based on the ligand pyc) was 86.5%.

Figure 8:
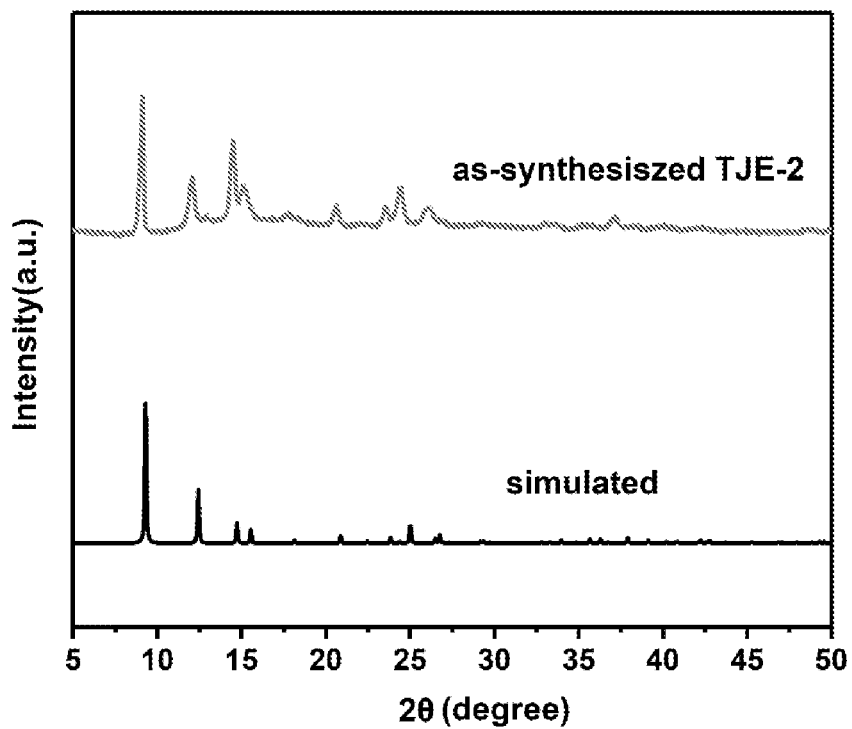
FIG. 8 shows the powder X-ray diffraction pattern for the scale-up synthesized TJE-2 in Example 3.

The material was analyzed using powder X-ray diffraction, and the results were consistent with the simulated result (FIG. 8), proving that the scaled-up synthesis was successful.

The foregoing embodiments are used only to illustrate the technical solutions of the present invention, but not to limit it. Although the present invention has been described in detail concerning the foregoing embodiments, it should be understood by those of ordinary skill in the art that 1) it is still possible to modify the technical solutions in the above embodiments or to replace some or all of the technical features with equivalent modifications or replacements; 2) these modifications or replacements do not make the essence of the corresponding technical solutions out of the scope of the present invention.

What is claimed is:

1. A metal-organic framework material for adsorptive separation of acetylene/ethylene mixture, wherein the metal-organic framework material is named TJE-2 with a chemical formula of $[Ni(pyc)_3(apyz)_2]_n$, wherein Ni represents nickel as a metal center, pyc represents an organic ligand 1H-pyrazole-4-carboxylic acid (structural formula:

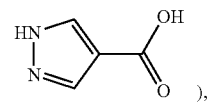

), and apyz represents an organic ligand 2-aminopyrazine (structural formula:

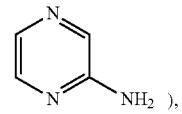

), and wherein the metal-organic framework material is 6-coordinated without forming open metal sites, each metal center being coordinated with:
one N atom from a first 1H-pyrazole-4-carboyxlic acid ligand,
one N atom from a second 1H-pyrazole-4-carboyxlic acid ligand,
two O atoms from a third 1H-pyrazole-4-carboyxlic acid ligand,
one N atom from a first 2-aminopyrazine ligand, and
one N atom from a second 2-aminopyrazine ligand.

2. The metal-organic framework material according to claim 1, wherein the metal-organic framework material TJE-2 has ultra-microporous periodic one-dimensional channels, wherein the pore diameter of the channels is 4.3-6, and wherein electronegative oxygen atoms, pyrazine rings and amino groups are distributed on the channel surface.

3.

A method for preparing the metal-organic framework material according to claim 1, comprising the following steps:
S1: dissolving the organic ligands 1H-pyrazole-4-carboxylic acid and 2-aminopyrazine in an organic solvent under stirring, and then adding and dissolving $Ni(NO_3)_2 \cdot 6H_2O$ into the organic solvent by stirring or ultrasonic vibration to obtain a mixture comprising the organic ligands and $Ni(NO_3)_2 \cdot 6H_2O$ dissolved in the organic solvent;

S2: transferring the mixture obtained in step S1 to a pressure-resistant closed container, and heating the mixture to 80-100° C. for 24-48 h;

S3: cooling the heated mixture to room temperature, obtaining a homogeneous powder material from the cooled mixture by filtration, and then solvent-exchanging the powder material with methanol;

S4: filtrating the solvent-exchanged powder material and then heating the filtrated solvent-exchanged powder material under vacuum at 80-100° C. for 24-48 h to completely remove solvent molecules in the channels, thereby obtaining the metal-organic framework material.

4. The method according to claim 3, wherein the molar ratio of the organic ligand 1H-pyrazole-4-carboxylic acid, the organic ligand 2-aminopyrazine, and $Ni(NO_3)_2 \cdot 6H_2O$ is 1:1-2:1-5 in step S1.

5. The method according to claim 3, wherein the organic solvent is composed of methanol and N,N-dimethylformamide, and the volume ratio of methanol to N,N-dimethylformamide in the organic solvent is 1:0.5-2 in step S1.

6. The method according to claim 3, wherein the closed container in step S2 is a closed glass reaction bottle with a polytetrafluoroethylene mat or a polytetrafluoroethylene-lined reaction kettle.

7. The method according to claim 3, wherein the solvent exchange is performed for not less than 4 days and not less than 8 times in step S3.

8. The method according to claim 3, wherein the suction filtration processes in steps S3 and S4 are conducted in a glass sand core suction filtration device or a Buchner funnel equipped with an organic phase filter membrane with a pore size of 0.2-0.8 μm.

9. A method for adsorptive separation of acetylene/ethylene mixture using the metal-organic framework material according to claim 1, comprising the following steps:

A1: loading the metal-organic framework material in a fixed bed adsorption column with an inner diameter of 6-10 mm, and then introducing a $C_2H_2/C_2H_4$ mixture at a flow rate of 2-10 mL/min at ambient temperature and pressure;

A2: allowing the metal-organic framework material to adsorb and capture the $C_2H_2$, thus separating $C_2H_2$ from $C_2H_4$, and obtaining a $C_2H_4$ gas with a purity of >99.9% from an exit of the adsorption column;

A3: after the metal-organic framework material reaches an uptake capacity, achieving regeneration of the metal-organic framework material by desorption under vacuum for 2-8 h or by heating and purging with inert gas.

10. The method for adsorptive separation of an acetylene/ethylene mixture according to claim 9, wherein the volume ratio of acetylene and ethylene in the $C_2H_2/C_2H_4$ mixture is 1:99 to 99:1.

* * * * *